(12) United States Patent
Rogers et al.

(10) Patent No.: US 12,179,472 B2
(45) Date of Patent: Dec. 31, 2024

(54) REINFORCED ADHESIVE SUBSTRATE

(71) Applicant: Solventum Intellectual Properties Company, Maplewood, MN (US)

(72) Inventors: John J. Rogers, Saint Paul, MN (US); Audrey A. Sherman, Woodbury, MN (US); Amanda C. Engler, Woodbury, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 17/767,461

(22) PCT Filed: Oct. 30, 2020

(86) PCT No.: PCT/IB2020/060240
§ 371 (c)(1),
(2) Date: Apr. 8, 2022

(87) PCT Pub. No.: WO2021/090136
PCT Pub. Date: May 14, 2021

(65) Prior Publication Data
US 2024/0083139 A1    Mar. 14, 2024

Related U.S. Application Data

(60) Provisional application No. 62/930,218, filed on Nov. 4, 2019.

(51) Int. Cl.
*B32B 7/12* (2006.01)
*B32B 7/03* (2019.01)
*B32B 37/12* (2006.01)

(52) U.S. Cl.
CPC .................. *B32B 7/12* (2013.01); *B32B 7/03* (2019.01); *B32B 37/12* (2013.01); *B32B 2260/021* (2013.01); *B32B 2307/412* (2013.01); *B32B 2307/54* (2013.01); *B32B 2307/718* (2013.01);
(Continued)

(58) Field of Classification Search
None
See application file for complete search history.

(56) References Cited

U.S. PATENT DOCUMENTS

| 24,906 A | 12/1960 | Ulrich et al. |
| 3,389,827 A | 6/1968 | Abere et al. |
| 3,645,835 A | 2/1972 | Hodgson et al. |

(Continued)

FOREIGN PATENT DOCUMENTS

| WO | 2003052018 A1 | 6/2003 |
| WO | 2009082602 A2 | 7/2009 |

(Continued)

OTHER PUBLICATIONS

International Search Report for PCT International Application No. PCT/IB2020/060240, mailed on Feb. 2, 2021, 4 pages.

*Primary Examiner* — Alexander S Thomas
(74) *Attorney, Agent, or Firm* — Mueting Raasch Group

(57) ABSTRACT

The disclosed reinforced adhesive substrate includes a transparent, flexible, breathable backing with a reinforcing material having open areas to the substrate. The reinforcing material strengthen the breathable backing while maintaining transparency so that overall the substrate is transparent. A transparent adhesive substrate can allow the underlying surface to be visualized.

14 Claims, 2 Drawing Sheets

(52) U.S. Cl.
CPC ... *B32B 2307/72* (2013.01); *B32B 2307/7376* (2023.05)

(56) References Cited

U.S. PATENT DOCUMENTS

| | | | |
|---|---|---|---|
| 4,112,213 | A | 9/1978 | Waldman et al. |
| 4,310,509 | A | 1/1982 | Berglund et al. |
| 4,323,557 | A | 4/1982 | Rosso et al. |
| 4,595,001 | A | 6/1986 | Potter et al. |
| 4,737,410 | A | 4/1988 | Kantner |
| 5,088,483 | A | 2/1992 | Heinecke |
| 6,461,467 | B2 | 10/2002 | Blatchford et al. |
| 6,685,682 | B1 | 2/2004 | Heinecke et al. |
| 2002/0187694 | A1* | 12/2002 | Brighton ............... B32B 27/12 442/41 |
| 2015/0238444 | A1 | 8/2015 | Menon et al. |
| 2018/0280591 | A1 | 10/2018 | Menon et al. |

FOREIGN PATENT DOCUMENTS

| | | | |
|---|---|---|---|
| WO | 2010056541 | A1 | 5/2010 |
| WO | 2010056543 | A1 | 5/2010 |

\* cited by examiner

REINFORCED ADHESIVE SUBSTRATE

CROSS REFERENCE TO RELATED APPLICATIONS

This application is a national stage filing under 35 U.S.C. 371 of PCT/IB2020/060240, filed Oct. 30, 2020, which claims the benefit of U.S. Provisional Application No. 62/930,218, filed Nov. 4, 2019, the disclosures of which are incorporated by reference in their entirety herein.

TECHNICAL FIELD

The present disclosure relates to a reinforced adhesive substrate.

BACKGROUND

Adhesive tapes and dressings are commonly used in medical applications. For example, at times, it may be necessary to insert tubes into a patient for different purposes, such as, feeding, air supply, and/or inserting or removing fluids. Tubes entering or exiting a body need to be securely attached to the patient's skin to maintain the correct position of the tube and can also function to keep the insertion site clean. Movement of these tubes in a patient can be uncomfortable therefore, tapes or adhesive dressings are commonly used to secure such tubes to the patient.

SUMMARY

The disclosed reinforced adhesive substrate includes a transparent, flexible, breathable backing with a reinforcing material having open areas to the substrate. The reinforcing material strengthen the breathable backing while maintaining transparency so that overall the substrate is transparent. A transparent adhesive substrate can allow the underlying surface to be visualized.

Existing film dressings are widely used on skin because they protect the skin by acting as a barrier to contaminating liquids and bacteria. For example, film dressings are available under a number of trade names such as TEGADERM™ (3M Company, St. Paul, MN). The polymeric films used in those dressings and drapes are conformable, i.e., the films are extremely thin, flexible and supple. They are typically supplied with a releasable protective liner covering the adhesive coated surface of the film. To prevent the adhesive coated film from wrinkling during application, various delivery systems have been proposed to address this problem, such as those disclosed in U.S. Pat. No. 6,685,682.

Thin polymeric films that are flexible and resilient are beneficial when used on skin that flexes, stretches, and retracts. However, for some applications, the high flexibility and resiliency of the thin polymeric film can move and stretch too much causing the film to peel or release from the skin. Medical dressings have been developed that include stiffer, less conformable materials secured to the thin polymeric film. For example, U.S. Pat. No. 5,088,483 discloses an adhesive composite that includes a conformable backing and a permanent adhesive reinforcement around the periphery of the adhesive composite. For example, a commercially available medical dressing with a reinforcement layer is TEGADERM™ IV Advanced Dressing (3M Company, St. Paul MN). However, there still remains a need for a highly breathable, flexible, transparent reinforced materials.

In one embodiment, the reinforced substrate comprises a transparent backing having a first major surface and a second major surface, opposite the first major surface, a reinforcing material on the first major surface of the backing with open area to the backing, and an adhesive on the first major surface of the backing. The reinforced substrate is transparent.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention. The figures may not be drawn to scale.

DETAILED DESCRIPTION

Figure 1:
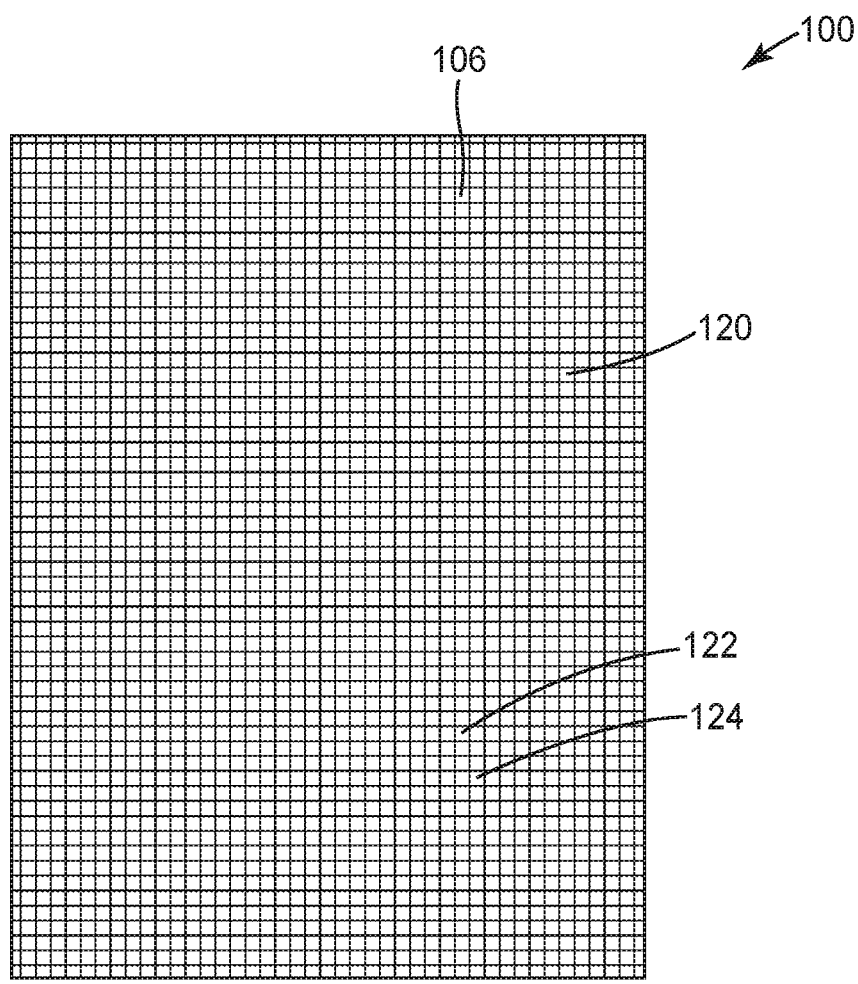
FIG. 1 is a front view of one embodiment of a reinforced substrate.
Figure 2:
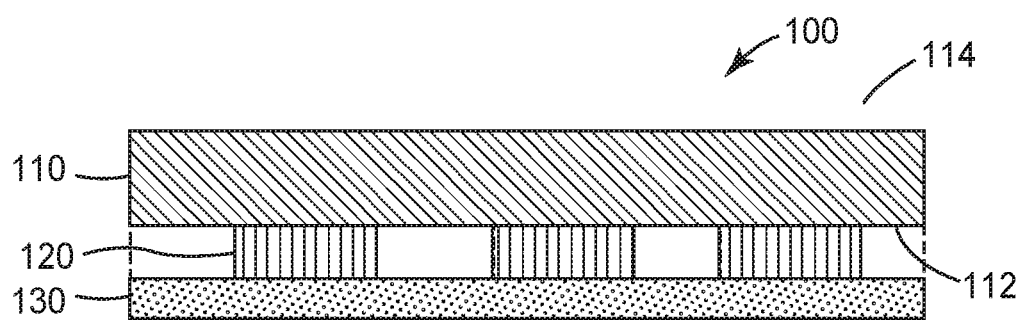
FIG. 2 is a cross sectional view of the reinforced substrate of FIG. 1.

FIG. 1 is a front view of one embodiment of a reinforced substrate 100, and FIG. 2 is a cross sectional view of the reinforced substrate 100 of FIG. 1. Overall, the reinforced substrate 100 is drapable, strong, non-extensible, moisture-vapor permeable, and transparent. The reinforced substrate 100 is well suited for application to skin. Therefore, the reinforced substrate 100 includes an adhesive. For example, the reinforced substrate 100 could be a bandage, a dressing, a tape, or a securement device.

In U.S. Pat. No. 6,461,467, the term "substantially contact transparent" is used to describe their articles and meaning that when adhered to a patient's skin, a wound or catheter site can be visually monitored through those portions of the backing and pressure sensitive adhesive or adhesives in contact with the patient's skin without requiring removal of the dressing. As used herein, the term transparent refers to an article, film, or adhesive that one can view an object through with the naked eye without the object being distorted or obscured. Transparency can be measured in a number of ways. For example, luminous transmission, clarity, or haze are measures of transparence. In one embodiment, the reinforced substrate may have a % luminous transmission (% T) over at least a portion of the visible light spectrum (about 400 to about 700 nm) of at least 50%, at least 70%, or at least 85%. In one embodiment, the reinforced substrate may have a haze over at least a portion of the visible light spectrum of less than 60%, less than 50%, or less than 40% and generally greater than at least 10%, or greater than at least 20%. In one embodiment, the reinforced substrate may have a clarity over at least a portion of the visible light spectrum of at least 20%, at least 30%, or at least 50%. Luminous transmission, clarity and haze can be measured according to ASTM D1003-00, such as using a Gardner Haze-Guard Plus model 4725 (available from BYK-Gardner, Columbia, MD).

The reinforced substrate 100 has a backing 110 with a first major surface 112 and a second major surface 114, opposite the first major surface 112. The backing 110 is a flexible, drapable, and transparent material. In one embodiment, the backing 110 is a polyurethane film.

Adjacent to the first major surface 112 of the backing 110 is a reinforcing material 120. The reinforcing material 120 is non-extensible in at least one direction to limit extensibility of the backing 110. Typically, the reinforcing material 120 is non-extensible in at least two directions. The reinforcing material 120 is secured to the backing 110. Typically, the reinforcing material 120 can be secured to the backing 110 by adhesive or a thermal bond.

In the embodiment shown in FIG. 1 and FIG. 2 the reinforcing material 120 comprises a first fiber 122 in a first direction, extending left to right in FIG. 1, and a second fiber 124 in a second direction, extending top to bottom in FIG. 1. The reinforcing material 120 restricts extensibility of the backing 110. Therefore, in this embodiment, the reinforcing material 120 restricts extensibility in the first and second directions of the first and second fibers 122, 124. In this embodiment, the first and second direction of the first and second fibers 122, 124 are arranged 90 degrees relative to one another. In other embodiment, the first and second direction of the first and second fibers 122, 124 are arranged from 45 to 90 degrees relative to one another. Other arrangements of the reinforcing material 120 could be depending on the extensibility limitations.

The reinforcing material 120 is secured to the backing 110 with open areas 106 between the fibers 122, 124. These open areas 106 provide for improved moisture vapor permeability. Further, the size of the open areas 106 relative to the reinforcing material 120 can be balanced to control for transparency of the overall reinforced substrate 100. In particular, in some embodiments, the reinforcing material 120 itself is transparent, therefore, a lower area of open areas 106 is needed to give transparency to the overall reinforced substrate 100. In some embodiment, if the reinforcing material 120 is less transparent, then a higher area of open areas 106 is needed to give transparency to the overall reinforced substrate 100. In one embodiment, there is at least 70% open areas on the reinforced substrate 100.

Transparency permits observation and inspection of objects (e.g., wound tissue, medical devices) disposed beneath the reinforced substrate 100. Therefore, a transparent reinforced substrate 100 provides visual inspection of objects (e.g., wound tissue, medical devices) disposed beneath the article to allows a caregiver to observe a wound over which a reinforced substrate 100 is applied without removing the reinforced substrate 100.

Figure 3:
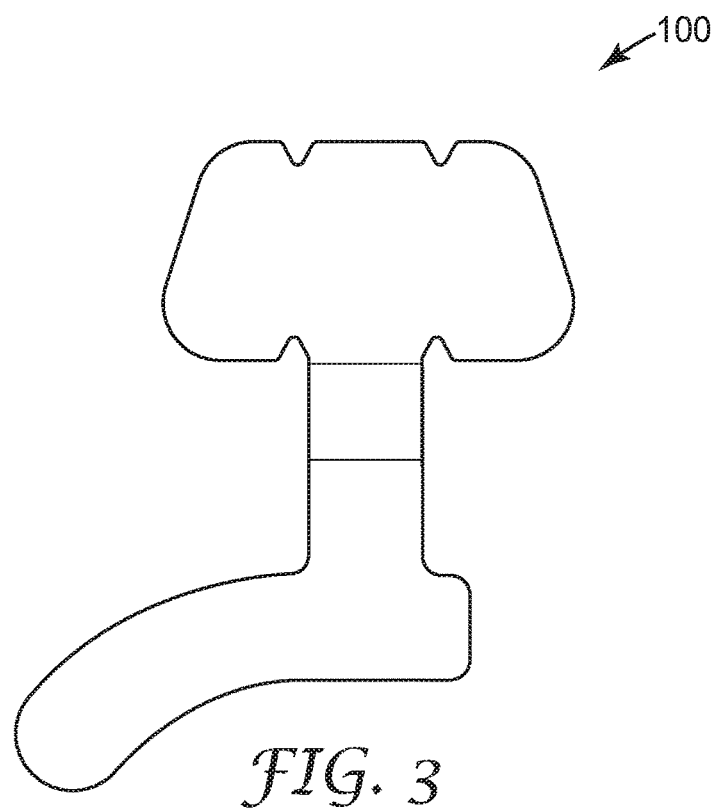
FIG. 3 is a front view of the reinforced substrate used as a tube securement device.
Figure 4:
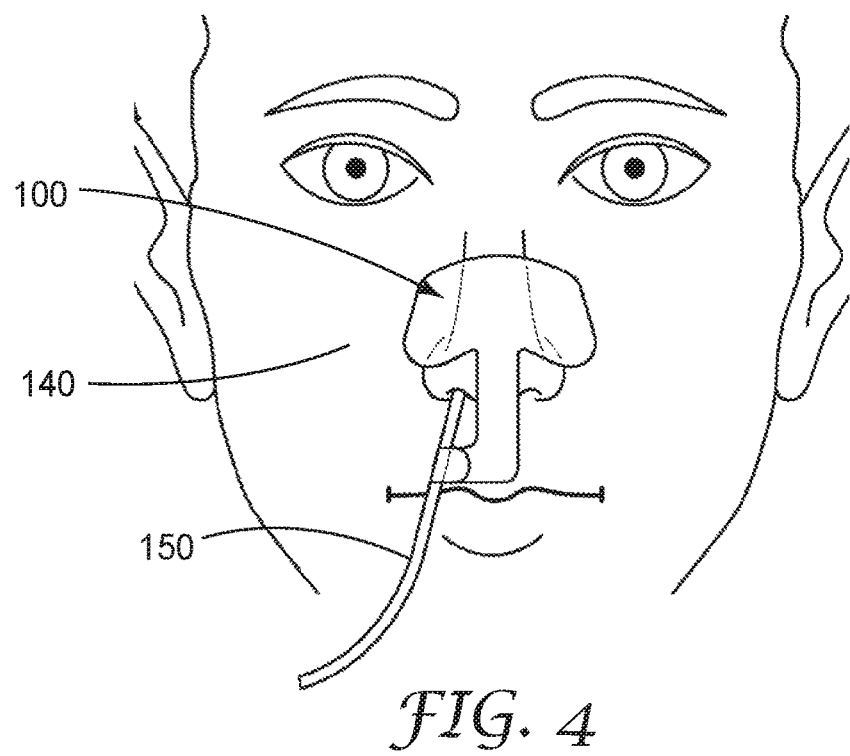
FIG. 4 is a perspective view of the reinforced substrate used as a tube securement device.

FIG. 3 is a front view of an embodiment of the reinforced substrate 100 formed in a shape to be used as a tube securement device. FIG. 4 is a perspective view of the reinforced substrate 100 securing a tube 150 to a surface 140, in this case a nose 140. The reinforced substrate 100 is the reinforced substrate described above in FIG. 1 and FIG. 2, but the reinforcing material 120 is not shown for drawing simplicity.

The transparent reinforced substrate 100 is well-suited for medical applications because it is clear, strong, and breathable. A transparent reinforced substrate 100 used for securement to a surface 140, such as skin, allows for visualization of the underlying surface. Therefore, if the skin is getting red, irritated, or infected, it will be apparent, and the treatment can follow.

Other applications include the transparent reinforced substrate for use on intravenous (IV) dressing, wound and ostomy care dressings, wearable medical devices or sensors like a blood glucose monitors.

Backing

The backing 110 is typically a thin-film material (single layer or multilayer). The backing may be coated with the adhesive. Typically, the thin film material provides resistance against incoming water and contaminants and has a high moisture vapor permeability to allow moisture vapor from the underlying skin to exit. One example of a suitable material is a high moisture vapor permeable film such as described in U.S. Pat. Nos. 3,645,835 and 4,595,001, the disclosures of which are herein incorporated by reference. Issued U.S. Pat. Nos. 3,645,835 and 4,595,001, the disclosures of which are hereby incorporated by reference, describe methods of making such films and methods for testing their permeability. Typically, the film/adhesive composite should transmit moisture vapor at a rate equal to or greater than human skin. Typically, the adhesive coated film transmits moisture vapor at a rate of at least 250 $g/m^2/24$ hrs/37° C./100-10% RH, more preferably at least 700 $g/m^2/24$ hrs/37° C./100-10% RH, and most preferably at least 2000 $g/m^2/24$ hrs/37° C./100-10% RH using the inverted cup method as described in U.S. Pat. No. 4,595,001.

The backing 110 is preferably conformable to anatomical surfaces. As such, when applied to an anatomical surface, it conforms to the surface even when the surface is moved and can stretch and retract. In one embodiment of a backing is an elastomeric polyurethane, polyester, or polyether block amide films. These films combine the desirable properties of resiliency, high moisture vapor permeability, and transparency. Example of material for the backing is in 3M Tegaderm IV Dressings available from 3M Company.

Commonly, a frame is included on the second major surface of the backing 110. The frame is made of a substrate that is less resilient than the film and may be removable from the film. Examples of materials and frames include those in 3M Tegaderm IV Dressings and 3M Tegaderm IV Advanced Dressings, both available from 3M Company.

Reinforcing Material

The reinforcing material 120 is less extensible than the backing 100.

For example, the reinforcing material 120 can have a tensile strength from 100 to 300 N/5 cm in the machine direction and from 100-300 in the cross-web direction. For example, the reinforcing material 120 can have an elongation from 20-30% in the machine direction and from 15-30% in the cross-web direction.

To allow for the overall reinforced substrate 100 to be flexible and conformable, the reinforcing material 120 typically is flexible and conformably in the x-y plane, or in other words is drapable. The reinforcing material 120 may be directly or indirectly in contact with the underlying surface, so to prevent pressure points or irritation to the underlying surface, the reinforcing material 120 is thin. In some embodiments, the reinforcing material 120 is from 100-300 microns.

To aid in processing, the reinforcing material 120 is a continuous web of material. In one embodiment, the reinforcing material 120 has a basis weight from 15 to 50 $g/m^2$.

In some embodiments, the reinforcing material 120 is a polymeric material that is thermoformable or a thermoplastic. For example, the reinforcing material 120 can be a polyolefin.

To aid in securing to the second surface 114 of the backing, the reinforcing material 120 can have a surface that is substantially planar. To aid in the overall reinforced substrate 100 to be transparent, the reinforcing material 120 itself may be transparent. A reinforcing material 120 that is itself transparent and with surfaces that are substantially planar further aid in the overall reinforced substrate 100 to be transparent. Nonplanar surfaces of the reinforcing material, such a round filaments, can distort the light transmitting through the material because of the gap that can form between the rounded edges of the filament over the surface to which it is secured. In addition, filaments have a high point that can create a pressure point and irritate the skin to which the reinforcing material is attached.

One example of a suitable material for use as the reinforcing material 120 is a cross laminated polyolefin open mesh nonwoven. For example, CLAF™ fabric is suitable as the reinforcing material.

Adhesive

The adhesive 130 used on the reinforced substrate 100 is typically a pressure sensitive adhesive, such as an acrylate-based or silicone-based adhesive. For application of applying the reinforced substrate 100 to skin, the pressure sensitive adhesives in combination with the backing will transmit moisture vapor at a rate greater to or equal to that of human skin.

One example of a pressure sensitive acrylate adhesive that can be applied to skin is described in U.S. Pat. No. RE 24,906, the disclosure of which is hereby incorporated by reference. In one embodiment, a 97:3 iso-octyl acrylate:acrylamide copolymer adhesive can be used or a 70:15:15 isooctyl acrylate:ethyleneoxide acrylate:acrylic acid terpolymer, as described in U.S. Pat. No. 4,737,410 (Example 31), the disclosure of which is hereby incorporated by reference. Other useful adhesives are described in U.S. Pat. Nos. 3,389,827, 4,112,213, 4,310,509, and 4,323,557, the disclosures of which are hereby incorporated by reference. Silicone adhesive can also be used. Generally, silicone adhesives can provide suitable adhesion to skin while gently removing from skin. Suitable silicone adhesives are disclosed in PCT Publications WO2010/056541 and WO2010/056543, the disclosure of which are herein incorporate by reference.

US Patent Application Publications 2018/0280591 and 2015/0238444, the disclosure of which are herein incorporated by reference, disclose antimicrobial agents dispersed throughout an adhesive composition. For example, chlorohexidine gluconate can be included within the pressure-sensitive acrylate adhesive to provide continuous antimicrobial activity.

The adhesive 130 can be applied in a continuous coating to the first major surface 112 of the backing. In some embodiments, the adhesive 130 may be applied in a pattern, as described in U.S. Pat. No. 4,595,001 which is hereby incorporated by reference. Also, it is understood that the entire first major surface 112 may include adhesive or the adhesive may be at select portions.

Optionally a release liner (not shown) may be used to cover the adhesive prior to use. During use, the release liner is removed, exposing the adhesive. Release liners can be made of paper or films, such as kraft papers, polyethylene, polypropylene, polyester or composites of any of these materials. The release liners are typically coated with release agents such as fluorochemicals or silicones.

Although specific embodiments have been shown and described herein, it is understood that these embodiments are merely illustrative of the many possible specific arrangements that can be devised in application of the principles of the invention. Numerous and varied other arrangements can be devised in accordance with these principles by those of skill in the art without departing from the spirit and scope of the invention. The scope of the present invention should not be limited to the structures described in this application, but only by the structures described by the language of the claims and the equivalents of those structures.

What is claimed is:

1. A reinforced substrate for application to skin, comprising:
   a transparent backing having a first major surface and a second major surface, opposite the first major surface, wherein the transparent backing comprises a film comprising a material selected from the group consisting of polyurethane, polyester, and polyether;
   a transparent reinforcing material that is less extensible than the transparent backing and comprises a grid forming multiple open areas, wherein the transparent reinforcing material comprises a first planar surface and a second planar surface opposing the first planar surface and adjacent to the first major surface of the transparent backing; and
   an adhesive on the first major surface of the transparent backing and the first planar surface of the transparent reinforcing material;
   wherein the reinforced substrate has a moisture vapor transmission rate (MVTR) of at least 250 $g/m^2/24$ hrs/37 degrees C./100-10% RH using the inverted cup method; and
   wherein the reinforced substrate has a percent luminous transmission (% T) over at least a portion of the visible light spectrum (400 to 700 nm) of at least 50%, a haze of between 10% and 60%, and a clarity of at least 20%.

2. The reinforced substrate of claim 1, wherein the reinforced substrate has a moisture vapor transmission rate (MVTR) of at least 700 $g/m^2/24$ hrs/37 degrees C./100-10% RH using the inverted cup method.

3. The reinforced substrate of claim 1, wherein the transparent reinforcing material comprises a first fiber extending in a first direction and a second fiber extending in a second direction, nonparallel with the first direction.

4. The reinforced substrate of claim 3, wherein the first direction is from 45 to 90 degrees relative to the second direction.

5. The reinforced substrate of claim 3, wherein the first fiber and second fiber are structurally connected together, independent from the backing.

6. The reinforced substrate of claim 1, wherein up to 70% of the transparent reinforcing material comprises the multiple open areas.

7. The reinforced substrate of claim 1, wherein the transparent reinforcing material has a thickness of 100 to 300 microns.

8. The reinforced substrate of claim 1, wherein the transparent reinforcing material has a basis weight from 15 to 50 $g/m^2$.

9. The reinforced substrate of claim 1, wherein the transparent reinforcing material has a tensile strength from 100 to 300 N/50 mm.

10. The reinforced substrate of claim 1, wherein the transparent reinforcing material is a thermally bonded to the transparent backing.

11. The reinforced substrate of claim 1, wherein the adhesive comprises a pressure sensitive adhesive, and wherein the adhesive is disposed over substantially all of the first major surface of the transparent backing.

12. The reinforced substrate of claim 1, wherein the reinforced substrate comprises:
   a first portion for securing to skin; and
   a second portion for securing to a medical device,
   wherein the transparent reinforcing material extends between the first portion and the second portion.

13. The reinforced substrate of claim 12, wherein the transparent reinforcing material extends over the first portion and second portion.

14. The reinforced substrate of claim 1, wherein the reinforced substrate comprises:
   a percent luminous transmission (% T) over at least a portion of the visible light spectrum (400 to 700 nm) of at least 70%;
   a haze of between 20% and 50%; and
   a clarity of at least 30%.

* * * * *